United States Patent
Takaya et al.

[11] Patent Number: 4,868,174
[45] Date of Patent: Sep. 19, 1989

[54] 3,7-DISUBSTITUTED-3-CEPHEM COMPOUNDS

[75] Inventors: Takao Takaya, Kawanishi; Yoshiko Inamoto, Uenonishi, both of Japan

[73] Assignee: Fujisawa Pharmaceutical Co., Ltd., Osaka, Japan

[21] Appl. No.: 8,330

[22] Filed: Jan. 29, 1987

[30] Foreign Application Priority Data

Mar. 17, 1986 [GB] United Kingdom ................ 8606544
Jun. 2, 1986 [GB] United Kingdom ................ 8613268
Oct. 14, 1986 [GB] United Kingdom ................ 8624558

[51] Int. Cl.$^4$ ................ C07D 501/46; A61K 31/545
[52] U.S. Cl. ................ 514/202; 540/222
[58] Field of Search ................ 540/222; 514/202

[56] References Cited

U.S. PATENT DOCUMENTS

| | | | |
|---|---|---|---|
| 4,152,432 | 5/1979 | Heymes et al. | 540/219 X |
| 4,406,899 | 9/1983 | Aburaki et al. | 540/722 X |
| 4,515,789 | 5/1985 | Metzger et al. | 540/222 X |
| 4,525,473 | 6/1985 | Aburaki et al. | 514/202 |

*Primary Examiner*—Nicholas S. Rizzo
*Attorney, Agent, or Firm*—Oblon, Spivak, McClelland, Maier & Neustadt

[57] ABSTRACT

The invention relates to an antimicrobial agent of the formula:

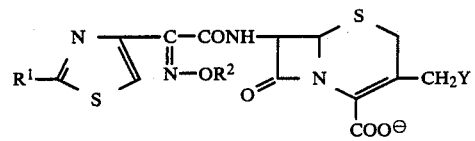

wherein $R^1$ is amino or conventional protected amino, $R^2$ is hydrogen or tetrahydropyranyl, and

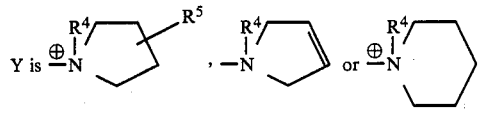

wherein $R^4$ is lower alkyl, and $R^5$ is hydrogen or lower alkyl substituted with hydroxy or conventional protected hydroxy, and pharmaceutically acceptable salts thereof.

15 Claims, No Drawings

3,7-DISUBSTITUTED-3-CEPHEM COMPOUNDS

The present invention relates to novel 3,7-disubstituted-3-cephem compounds and a pharmaceutically acceptable salt thereof.

More particularly, it relates to novel 3,7-disubstituted-3-cephem compounds and a pharmaceutically acceptable salt thereof, which have antimicrobial activity, to processes for the production of the same, to a pharmaceutical composition comprising the same, and to a method for the treatment of infectious diseases caused by pathogenic microorganisms comprising administering the same to infected human being or animals.

Accordingly, one object of the present invention is to provide novel 3,7-disubstituted-3-cephem compounds and a pharmaceutically acceptable salt thereof, which are highly active against a number of pathogenic microorganisms and are useful as antimicrobial agents.

Another object of the present invention is to provide processes for the production of novel 3,7-disubstituted-3-cephem compounds and a salt thereof.

A further object of the present invention is to provide a pharmaceutical composition comprising, as an active ingredient, said 3,7-disubstituted-3-cephem compounds and a pharmaceutically acceptable salt thereof.

Still further object of the present invention is to provide a method for the treatment of infectious diseases caused by pathogenic microorganisms which comprises administering said 3,7-disubstituted-3-cephem compounds and a pharmaceutically acceptable salt thereof to the infected human being or animals.

The 3,7-disubstituted-3-cephem compounds according to this invention are novel and can be represented by the following general formula (I).

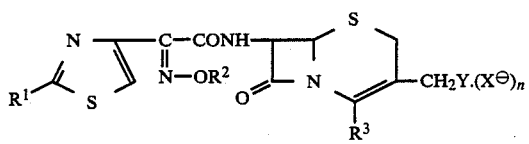

(I)

wherein
$R^1$ is amino or protected amino,
$R^2$ is hydrogen or hydroxy protective group,
$R^3$ is carboxy, $COO^\ominus$ or protected carboxy, Y is wherein
$R^4$ is lower alkyl, and
$R^5$ is hydrogen or lower alkyl substituted with hydroxy or protected hydroxy,
X is acid residue, and
n is 0 or 1,
with the proviso that when $R^3$ is $COO^\ominus$, then n is 0, and when $R^3$ is carboxy or protected carboxy, then n is 1.

It is to be understood that the term "syn isomer" used in the present specification means the compound (I) having the stereospecific partial structure of the formula:

$$-\underset{\underset{N-OR^2}{\|}}{C}-CO-$$

wherein $R^2$ is as defined above.

Suitable pharmaceutically acceptable salts of the object compounds (I) are conventional non-toxic salts and may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, dibenzylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like.

The object compound (I) or a pharmaceutically acceptable salt thereof of this invention can be prepared by the processes illustrated below.

Process 1:

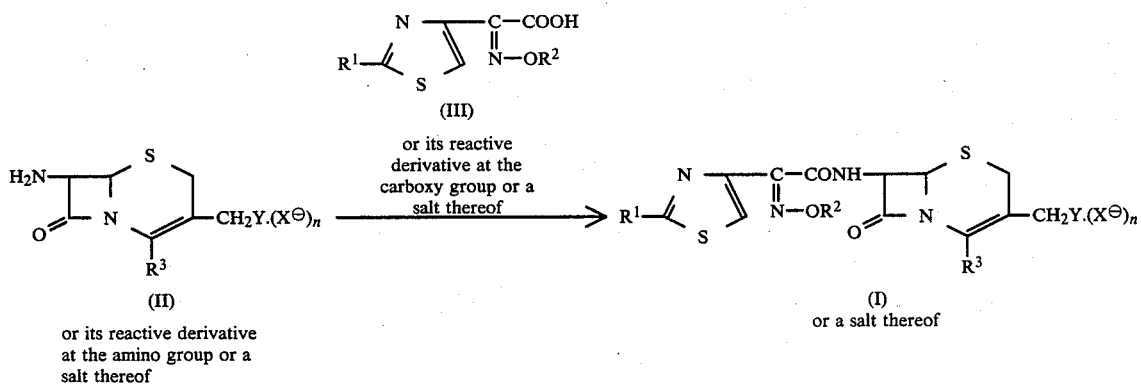

Process 2:

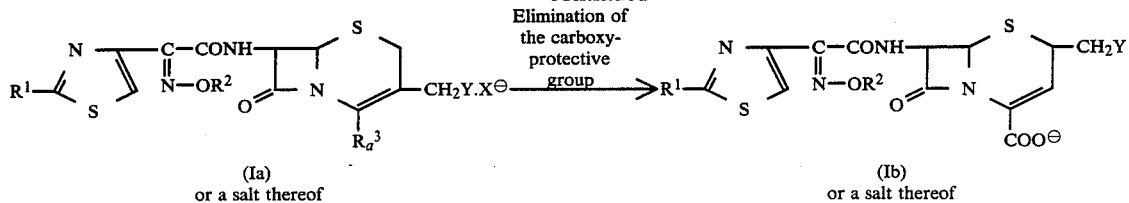

(Ia) or a salt thereof → (Ib) or a salt thereof
Elimination of the carboxy-protective group Process 3:

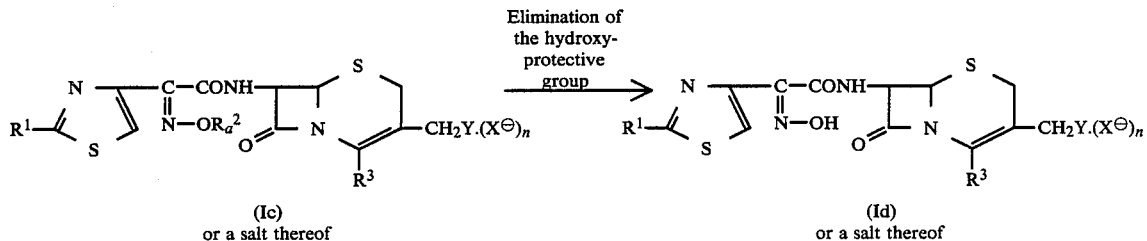

(Ic) or a salt thereof → (Id) or a salt thereof
Elimination of the hydroxy-protective group Process 4:

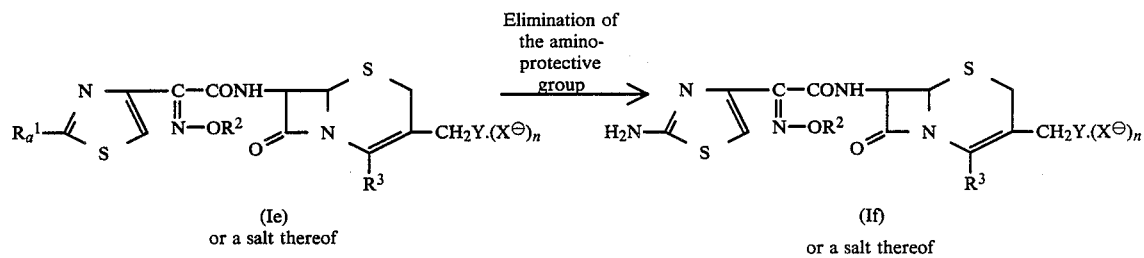

(Ie) or a salt thereof → (If) or a salt thereof
Elimination of the amino-protective group Process 5:

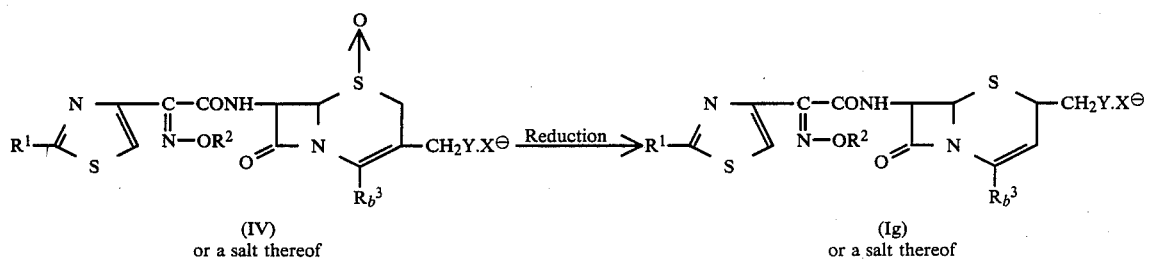

(IV) or a salt thereof → (Ig) or a salt thereof
Reduction wherein
$R^1$, $R^2$, $R^3$, X, Y and n are each as defined above,
$R_a^1$ is protected amino,
$R_a^2$ is hydroxy protective group,
$R_a^3$ is protected carboxy, and
$R_b^3$ is carboxy or protected carboxy.

Among the starting compounds in the present invention, the compound (IV) is novel, and the compounds (IIa), (IIb) and (IV) can be prepared by the processes which are illustrated in the following schemes or by a conventional method.

Process A:

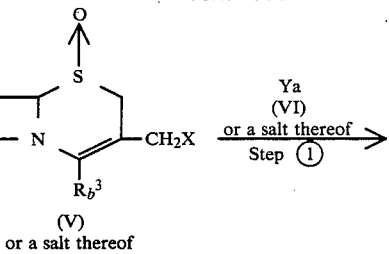

(V) or a salt thereof
Ya (VI) or a salt thereof
Step ①

-continued

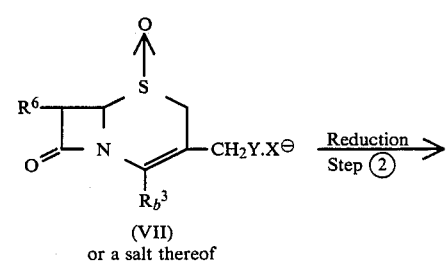

(VII) or a salt thereof
Reduction
Step ②

-continued

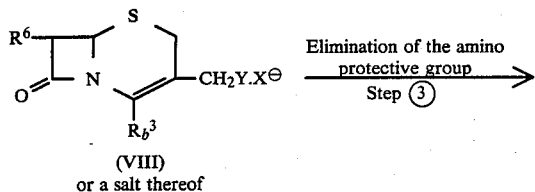

(VIII) or a salt thereof

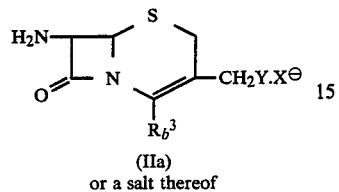

(IIa) or a salt thereof

Process B:

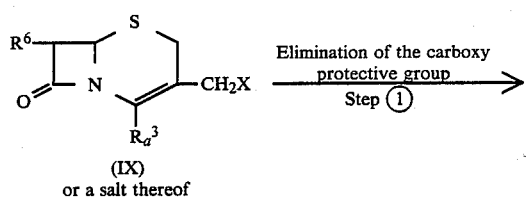

(IX) or a salt thereof

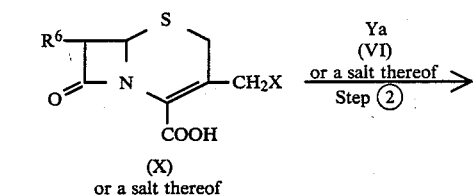

(X) or a salt thereof

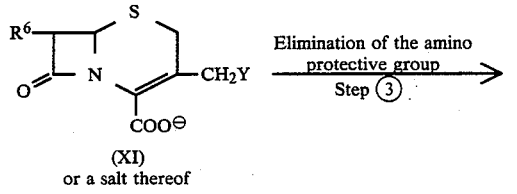

(XI) or a salt thereof

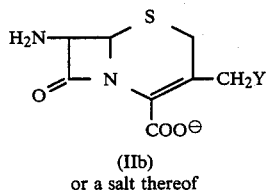

(IIb) or a salt thereof

Process C:

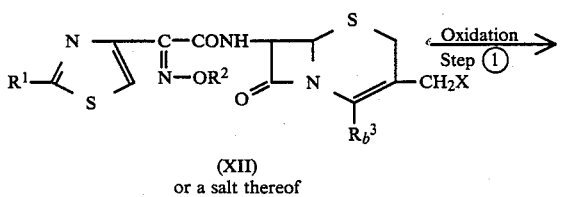

(XII) or a salt thereof

-continued

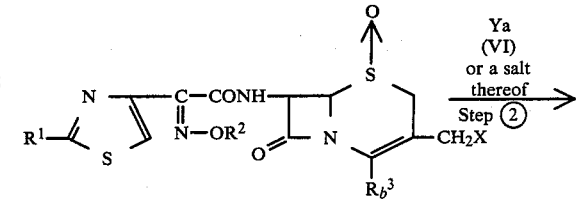

(XIII) or a salt thereof

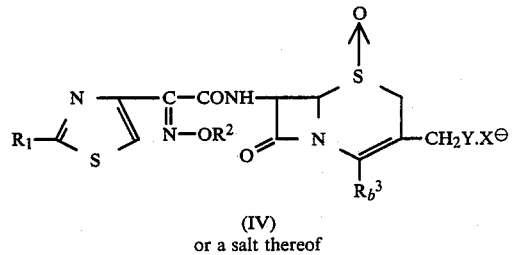

(IV) or a salt thereof wherein $R^1$, $R^2$, $R_a{}^3$, X and Y are each as defined above,

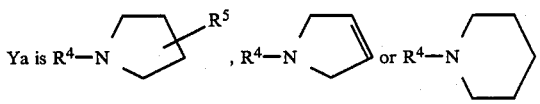

wherein $R^4$ and $R^5$ are each as defined above, and $R^6$ is protected amino.

In the above and subsequent descriptions of the present specification, suitable examples and illustrations of the various definitions which the present invention includes within the scope thereof are explained in detail as follows.

The term "lower" is intended to mean 1 to 6 carbon atom(s), unless otherwise indicated.

The term "higher" is intended to mean 7 to 20 carbon atoms, unless otherwise indicated.

Suitable "protected amino" group may include an amino group substituted by a conventional amino-protective group which is used in penicillin and cephalosporin compounds, for examples, acyl as mentioned below, ar(lower)alkyl such as mono-(or di or tri)-phenyl(lower)alkyl (e.g. benzyl, benzhydryl, trityl, etc.), lower alkoxycarbonyl(lower)alkylidene or its enamine tautomer (e.g. 1-methoxycarbonyl-1-propen-2-yl, etc.), di(lower)alkylaminomethylene (e.g. dimethylaminomethylene, etc.), etc.

Suitable "acyl" may include carbamoyl, an aliphatic acyl, an aromatic acyl, a heterocyclic acyl and an aliphatic acyl substituted with aromatic or heterocyclic group(s).

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, tert-butoxycarbonyl, etc.), lower alkenoyl (e.g. acryloyl, methacryloyl, crotonoyl, etc.), $(C_3-C_7)$-cycloalkanecarbonyl (e.g. cyclohexanecarbonyl, etc.), amidino, and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclecarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include ar(lower)alkanoyl such as phenyl(lower)alkanoyl (e.g. phenylacetyl, phenylpropionyl, phenylhexanoyl, etc.), ar(lower)alkoxycarbonyl such as phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with one or more suitable substituents such as lower alkyl, (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro and the like, and preferable acyl having such substituent(s) may be mono (or di or tri)halo(lower)alkanoyl (e.g. chloroacetyl, bromoacetyl, dichloroacetyl, trifluoroacetyl, etc.), mono (or di or tri)halo(lower)alkoxycarbonyl (e.g. chloromethoxycarbonyl, dichloromethoxycarbonyl, 2,2,2-tri-chloroethoxycarbonyl, etc.), nitro (or halo or lower alkoxy)phenyl(lower)alkoxycarbonyl, (e.g. nitrobenzyloxycarbonyl, chlorobenzyloxycarbonyl, methoxybenzyloxycarbonyl, etc.), and the like.

Suitable "protected carboxy" may include an esterified carboxy group which is conventionally used in penicillin or cephalosporin compound.

Suitable "ester moiety" in "esterified carboxy" may include lower alkyl ester (e.g. methyl ester, ethyl ester, propyl ester, isopropyl ester, butyl ester, isobutyl ester, t-butyl ester, pentyl ester, tertpentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower)alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl ester, isopropylthiomethyl ester, etc.), carboxy-substituted-lower alkyl ester (e.g. carboxymethyl ester, 2-carboxyethyl ester, 3-carboxypropyl ester, etc.), protected carboxy-substituted-lower alkyl ester such as lower alkoxycarbonyl-substituted-lower alkyl ester (e.g. tert-butoxycarbonylmethyl ester, 2-tert-butoxycarbonylethyl ester, 3-tert-butoxycarbonylpropyl ester, etc.), mono(or di or tri)halo(lower)alkyl ester (e.g. 2-iodoethyl ester, 2,2,2-trichloroethyl ester, etc.), lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.], higher alkanoyloxy(lower)alkyl ester [e.g. heptanoyloxymethyl ester, octanoyloxymethyl ester, nonanoyloxymethyl ester, decanoyloxymethyl ester, undecanoyloxymethyl ester, lauroyloxymethyl ester, tridecanoyloxymethyl ester, myristoyloxymethyl ester, pentadecanoyloxymethyl ester, palmitoyloxymethyl ester, heptadecanoyloxymethyl ester, stearoyloxymethyl ester, nondecanoyloxymethyl ester, eicosanoyloxymethyl ester, 1(or 2)-heptanoyloxyethyl ester, 1(or 2)-octanoyloxyethyl ester, 1(or 2)-nonanoyloxyethyl ester, 1(or 2)-decanoyloxyethyl ester, 1(or 2)-undecanoyloxyethyl ester, 1(or 2)-lauroyloxyethyl ester, 1(or 2)-tridecanoyloxyethyl ester, 1(or 2)-myristoyloxyethyl ester, 1(or 2)-pentadecanoyloxy ethyl ester, 1(or 2)-palmitoyloxyethyl ester, 1(or 2)-heptadecanoyloxyethyl ester, 1(or 2)-stearoyloxyethyl ester, 1(or 2)-nonadecanoyloxyethyl ester, 1(or 2)-eicosanoyloxyethyl ester, etc.], lower alkoxycarbonyloxy(lower)alkyl ester [e.g. methoxycarbonyloxymethyl ester, ethoxycarbonyloxymethyl ester, propoxycarbonyloxymethyl ester, isopropoxycarbonyloxymethyl ester, tert-butoxycarbonyloxymethyl ester, 1(or 2)-methoxycarbonyloxyethyl ester, 1(or 2)-ethoxycarbonyloxyethyl ester, 1(or 2)-propoxycarbonyloxyethyl ester, 1(or 2)-isopropoxycarbonyloxyethyl ester, 1(or 2)-butoxycarbonyloxyethyl ester, 1(or 2)-isobutoxycarbonyloxyethyl ester, 1(or 2)-tert-butoxycarbonyloxyethyl ester, 1(or 2)-hexyloxycarbonyloxyethyl ester, 1(or 2 or 3)-methoxycarbonyloxypropyl ester, 1(or 2 or 3)-ethoxycarbonyloxypropyl ester, 1(or 2 or 3)-isopropoxycarbonyloxypropyl ester, 1(or 2 or 3 or 4)-ethoxycarbonyloxybutyl ester, 1(or 2 or 3 or 4)-butoxycarbonyloxybutyl ester, 1(or 2 or 3 or 4 or 5)-pentyloxycarbonyloxypentyl ester, 1(or 2 or 3 or 4 or 5)-neopentyloxycarbonyloxypentyl ester, 1(or 2 or 3 or 4 or 5 or 6)-ethoxycarbonyloxyhexyl ester, etc.], (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.], lower alkanesulfonyl(lower)alkyl ester (e.g. mesylmethyl ester, 2-mesylethyl ester, etc.), ar(lower)alkyl ester which may have one or more substituent(s) such as mono-(or di or tri)phenyl(lower)alkyl ester which may have one or more suitable substituent(s) (e.g. benzyl ester, 4-methoxybenzyl ester, 4-nitrobenzyl ester, phenethyl ester, benzhydryl ester, trityl ester, bis(methoxyphenyl)methyl ester, 3,4-dimethoxybenzyl ester, 4-hydroxy-3,5-di-t-butylbenzyl ester, etc.), aryl ester which may have one or more suitable substituents (e.g. phenyl ester, tolyl ester, t-butylphenyl ester, xylyl ester, mesityl ester, cumenyl ester, salicyl ester, etc.), heterocyclic ester (e.g. phthalidyl ester, etc.), and the like.

Suitable "halogen" may include chlorine, bromine, iodine, and the like.

Suitable "lower alkyl" may include straight or branched one having 1 to 6 carbon atom(s), such as methyl, ethyl, propyl, isopropyl, butyl, t-butyl, pentyl, hexyl or the like, and preferred is one having 1 to 3 carbon atom(s).

Suitable "acid residue" may include acyloxy, azido, halogen and the like, wherein acyl moiety in the term "acyloxy" and halogen can be referred to the ones as exemplified above.

Suitable "hydroxy-protective group" or "hydroxy-protective group" in "protected hydroxy" may include aforesaid acyl, ar(lower)alkyl (e.g. benzyl, trityl, etc.), lower alkoxy(lower)alkyl (e.g. 1-methyl-1-methoxyethyl, methoxypropyl, etc.), tetrahydropyranyl and the like.

Preferred embodiments of the object compounds (I) are as follows.

Preferred embodiments of $R^1$ is amino or ar(lower)alkylamino, more preferably amino or mono(or di or tri)phenyl(lower)alkylamino, most preferably amino or tritylamino;

$R^2$ is hydrogen, acyl, ar(lower)alkyl, lower alkoxy(lower)alkyl or tetrahydropyranyl, more preferably hydrogen or tetrahydropyranyl;

$R^3$ is carboxy, $COO^\ominus$, ar(lower)alkoxycarbonyl, more preferably carboxy, $COO^\ominus$ or benzhydryloxycarbonyl;

Y is 1-methyl-1-pyrrolidinium, 1-ethyl-1-pyrrolidinium, 1-methyl-1-piperidinium, 1-methyl-1-(3-pyrrolinium), 1-methyl-2-hydroxymethyl-1-pyrrolidinium, 1-methyl-2-carbamoyloxymethyl-1-pyrrolidinium or 1-methyl-2-hydroxyethyl-1-pyrrolidinium.

The processes for preparing the object compounds of the present invention are explained in detail in the following.

Process 1:

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl) acetamide, mono(trimethylsilyl)acetamide or the like; a derivative formed by reaction of the compound (II) with phosphorus trichloride or phosgene, and the like.

Suitable salt of the compounds (II) and (III) may include an acid addition salt such as an organic acid salt (e.g. acetate, maleate, tartrate, benzenesulfonate, toluenesulfonate, etc.) or an inorganic acid salt (e.g. hydrochloride, hydrobromide, sulfate, phosphate, etc.); a metal salt (e.g. sodium salt, potassium salt, calcium salt, magnesium salt, etc.); ammonium salt, an organic amine salt (e.g. triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl $[(CH_3)_2N^+=CH-]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

The present reaction includes, within its scope, the case that the hydroxy-protective group for $R^2$ is eliminated during the reaction or the post-treating step of the present process.

Process 2:

The compound (Ib) or a salt thereof can be prepared by subjecting the compound (Ia) or a salt thereof to elimination reaction of the carboxy-protective group.

Suitable salts of the compounds (Ia) and (Ib) may include the same ones as exemplified for the compound (I).

Suitable method for this elimination reaction may include conventional one such as hydrolysis, reduction, or the like.

(i) For hydrolysis:

Hydrolysis is preferably carried out in the presence of an acid.

Suitable acid may be an inorganic acid (e.g. hydrochloric acid, hydrobromic acid, sulfuric acid, etc.), an organic acid (e.g. formic acid, acetic acid, trifluoroacetic acid, propionic acid, methanesulfonic acid, benzenesulfonic acid, p-toluenesulfonic acid, etc.), an acidic ion-exchange resin and the like. In case that the organic acid such as trifluoroacetic acid and p-toluenesulfonic acid is used in this reaction, the reaction is preferably carried out in the presence of cation trapping agents (e.g. anisole, etc.).

Further, instead of the above acid, Lewis acid such as boron trifluoride, boron trifluoride etherate, aluminum trichloride, antimony pentachloride, ferric chloride, stannic chloride, titanium tetrachloride, zinc chloride, and the like can also be used in this reaction, and in case of using Lewis acid, the reaction can preferably be carried out in the presence of cation trapping agent (e.g. anisole).

The hydrolysis is usually conducted in a conventional solvent which does not adversely influence the reaction such as water, methanol, ethanol, propanol, tert-butyl alcohol, tetrahydrofuran, N,N-dimethylformamide, N,N-dimethylacetamide, dioxane, methylene chloride or a mixture thereof, and further the abovementioned acids can also be used as a solvent when they are in liquid.

The reaction temperature of this hydrolysis is not critical, and the reaction is usually conducted under cooling to at somewhat elevated temperature.

(ii) For Reduction:

Reduction is conducted in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobomic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction is usually conducted in a conventional solvent which does not adversely influence the reaction such as water, methanol, ethanol, propanol, N,N-dimethylformamide, or a mixture thereof. Additionally, in case that the abovementioned acids to be used in chemical reduction are in liquid, they can also be used as a solvent. Further, a suitable solvent to be used in catalytic reduction may be the abovementioned solvent, and other conventional solvent such as diethyl ether, dioxane, tetrahydrofuran, etc., or a mixture thereof.

The reaction temperature of this reduction is not critical and the reaction is usually conducted under cooling to warming.

The present elimination reaction of the carboxy protective group includes, within its scope, the cases that protected amino for $R^1$ is converted into the free amino or hydroxy protective group for $R^2$ is eliminated at the same time during the reaction or the post-treating step of the present process.

Process 3:

The compound (Id) or a salt thereof can be prepared by subjecting the compound (Ic) or a salt thereof to elimination reaction of the hydroxy-protective group.

Suitable salt of the compounds (Ic) and (Id) may include the same ones as exemplified for the compound (I).

This elimination reaction of the hydroxy-protective group of the compound (Ic) can be carried out in a similar manner to that of the aforementioned Process 2, and therefore the reagents to be used and the reaction conditions (e.g. solvent, reaction temperature, etc.) are referred to those of the Process 3.

The present elimination reaction includes, within its scope, the case that the protected amino for $R^1$ and/or protected carboxy group(s) for $R^3$ are converted into the corresponding free amino and/or free carboxy group(s) during the reaction or the post-treating step of the present process.

Process 4:

The compound (If) or a salt thereof can be prepared by subjecting the compound (Ie) or a salt thereof to elimination reaction of the amino-protective group.

Suitable salt of the compounds (Ie) and (If) may include the same ones as exemplified for the compound (I).

The present elimination reaction is carried out in accordance with a conventional method such as hydrolysis; reduction; elimination using Lewis acid; elimination method by reacting the compound (Ie) with iminohalogenating agent and then with iminoetherifying agent, and, if necessary, subjecting the resulting compound to hydrolysis; or the like.

Among these methods, "the elimination method by reacting the compound (Ie) with iminohalogenating agent and then with iminoetherifying agent, and, if necessary, subjecting the resulting compound to hydrolysis" is preferable method.

Suitable iminohalogenating agent may include phosphorus halide (e.g. phosphorus trichloride, phosphorus pentachloride, phosphorus tribromide, phosphorus pentabromide, etc.), phosphorus oxychloride, thionyl chloride, phosgene and the like. The reaction temperature is not critical, and the reaction is usually carried out under cooling or at ambient temperature.

In case that the compound (Ie) has a free carboxy group at the 4-position, this reaction is preferably carried out by protecting the free carboxy group with a silylating agent (e.g. trimethylsilyl chloride, trimethylsilylacetamide, bis(trimethylsilyl)acetamide, etc.) before this reaction.

Suitable iminoetherifying agent reacted with thus obtained reaction product may include an alcohol, metal alkoxide and the like. Suitable alcohol may include alkanol (e.g. methanol, ethanol, propanol, isopropanol, butanol, t-butanol, 1,3-butanediol, etc.) which may be substituted with alkoxy (e.g. methoxy, ethoxy, propoxy, isopropoxy, butoxy, etc.). Suitable metal alkoxide may include alkali metal alkoxide (e.g. sodium alkoxide, potassium alkoxide, etc.), alkaline earth metal alkoxide (e.g. calcium alkoxide, barium alkoxide, etc.) and the like. The reaction temperature is not critical, and the reaction is usually carried out under cooling or at ambient temperature. Thus obtained product is, if necessary, subjected to hydrolysis. The hydrolysis can readily be carried out by pouring the reaction mixture obtained above into water, but there may be previously added a hydrophilic solvent (e.g. methanol, ethanol, etc.), a base (e.g. alkali metal bicarbonate, trialkylamine etc.) or an acid (e.g. diluted hydrochloric acid, acetic acid, etc.) to the water.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present invention includes, within its scope, the case that the protected carboxy is transformed into the free carboxy group according to reaction conditions and kinds of the protective groups in the course of the reaction or in posttreatment. The hydrolysis may include a method using an acid or a base and the like. These methods may be selected depending on the kind of the acyl groups to be eliminated.

Suitable acid may include an organic or an inorganic acid, for example, formic acid, trifluoroacetic acid, benzenesulfonic acid, p-toluenesulfonic acid, hydrochloric acid and the like. The acid suitable for the reaction can be selected according to the kind of acyl group to be eliminated. When the elimination reaction is conducted with the acid, it can be carried out in the presence or absence of a solvent. Suitable solvent may include an organic solvent, water or a mixed solvent thereof. When trifluoroacetic acid is used, the elimination reaction may be preferably carried out in the presence of anisole.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,-2]octane, 1,5-diazabicyclo[5,4,0]undecene-5 or the like. The hydrolysis using a base is often carried out in water or a hydrophilic organic solvent or a mixed solvent thereof.

The reduction may include, for example, reduction with an alkali metal borohydride (e.g. sodium borohydride, etc.), catalytic reduction and the like.

The reaction temperature is not critical, and the reaction is usually carried out under cooling to warming.

The present elimination reaction includes, within its scope, the case that the protected carboxy group for $R^3$ is converted into the free carboxy group and the hydroxy-protective group for $R^2$ is eliminated at the same during the reaction or the post-treating step of the present process.

Process 5:

The compound (Ig) or a salt thereof can be prepared by reducing the compound (IV) or a salt thereof.

Suitable salt of the compounds (Ig) and (IV) may include the same ones as exemplified for the compound (I).

The present reduction can be carried out by a conventional method which is applied for the transformation of

into -S-, for example, by using phosphorus trichloride, a combination of stannous chloride and acetyl chloride, a combination of an alkali metal iodide (e.g. sodium iodide, etc.) and trihaloacetic anhydride (e.g. trifluoroacetic anhydride, etc.), and the like.

The present reduction is usually carried out in a solvent such as acetone, dioxane, acetonitrile, dimethylformamide, benzene, hexane, chloroform, methylene chloride, ethylene chloride, tetrahydrofuran, ethyl acetate, or any other solvent which does not adversely affect the reaction.

The reaction temperature is not critical and the reaction is usually carried out under cooling or at ambient temperature.

The processes for preparing the starting compounds of the present invention are explained in detail in the following.

Process A- ① :

The compound (VII) or a salt thereof can be prepared by reacting the compound (V) or a salt thereof with the compound (VI) or a salt thereof.

Suitable salt of the compounds (V), (VI) and (VII) can be referred to the ones exemplified for the compound (I).

The present reaction may be carried out in a solvent such as water, phosphate buffer, acetone, chloroform, acetonitrile, nitrobenzene, methylene chloride, ethylene chloride, formamide, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (V) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under heating. The present reaction is preferably carried out in the presence of alkali metal halide (e.g. sodium iodide, potassium iodide, etc.), alkali metal thiocyanate (e.g. sodium thiocyanate, potassium thiocyanate, etc.), etc.

Process A- ② :

The compound (VIII) or a salt thereof can be prepared by reducing the compound (VII) or a salt thereof.

Suitable salt of the compound (VIII) can be referred to the ones as exemplified for the compound (I).

The present reduction can be carried out in a similar manner to that of the aforementioned Process 5.

Process A- ② :

The compound (IIa) or a salt thereof can be prepared by subjecting the compound (VIII) or a salt thereof to elimination reaction of amino protective group.

Suitable salt of the compound (IIa) can be referred to the ones as exemplified for the compound (I).

This elimination reaction can be carried out in a similar manner to that of the aforementioned Process 2.

Process B- ① :

The compound (X) or a salt thereof can be prepared by subjecting the compound (IX) or a salt thereof to elimination reaction of the carboxy protective group.

Suitable salts of the compounds (IX) and (X) may include the same ones as exemplified for the compound (I).

This elimination reaction of the carboxy protective group of the compound (IX) can be carried out in a similar manner to that of the aforementioned Process 2.

Process B- ② :

The compound (XI) or a salt thereof can be prepared by reacting the compound (X) or a salt thereof with the compound (VI) or a salt thereof.

Suitable salts of the compound (XI) may include the same ones as exemplified for the compound (I).

This reaction can be carried out in a similar manner to that of the aforementioned Process A- ① .

Process B- ③ :

The compound (IIb) or a salt thereof can be prepared by subjecting the compound (XI) or a salt thereof to elimination reaction of the amino protective group.

Suitable salts of the compound (IIb) may include the same ones as exemplified for the compound (I).

This elimination reaction of the amino protective group of the compound (XI) can be carried out in a similar manner to that of the aforementioned Process 4.

Process C- ① :

The compound (XIII) or a salt thereof can be prepared by oxidizing the compound (XII) or a salt thereof.

Suitable salts of the compounds (XII) and (XIII) can be referred to the ones as exemplified for the compound (I).

The present oxidation reaction can be carried out by a conventional method which is applied for the transformation of -S- into

for example by using an oxidizing agent such as m-chloroperbenzoic acid, perbenzoic acid, peracetic acid, ozone, hydrogen peroxide, periodic acid or the like.

The present reaction is usually carried out in a solvent such as water, acetone, dioxane, acetonitrile, chloroform, methylene chloride, tetrahydrofuran, ethyl acetate or any other solvent which does not adversely affect the reaction.

The reaction temperature is not critical and the reaction is preferably carried out under cooling or at ambient temperature.

Process C- ② :

The compound (IV) or a salt thereof can be prepared by reacting the compound (XIII) or a salt thereof with the compound (VI) or a salt thereof.

The present reaction can be carried out in a similar manner to that of aforementioned Process A- ① .

The object compound (I) and the pharmaceutically acceptable salt thereof of the present invention are novel and exhibit high antimicrobial activity, inhibiting the growth of a wide variety of pathogenic microorganisms including Gram-positive and Gram-negative microorganisms and are useful as antimicrobial agents.

In order to illustrate the usefulness of the object compound, anti-microbial activities of same representative compounds of the present invention are shown below.

Minimal inhibitory concentrations (A) Test Method

In vitro antimicrobial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of μg/ml after incubation at 37° C. for 20 hours.

(B) Test Compounds (1) 7-[2-(2-Aminothiazol-4-yl)-2-hydroxyiminoacetamido]-3-(1-methyl-1-pyrrolidinio)methyl-3-cephem-4-carboxylate (syn isomer).

(2) 7-[2-Aminothiazol-4-yl)-2-hydroxyiminoacetamido]-3-(1-methyl-2-hydroxymethyl-1-pyrrolidinio)methyl-3-cephem-4-carboxylate (syn isomer).

(C) Test Results

| | M.I.C. (μg/ml) | |
|---|---|---|
| | Compounds | |
| Test strains | (1) | (2) |
| S. epidelmidis 89 | 0.39 | 0.78 |
| E. coli 31 | 0.20 | 0.10 |
| P. mirabilis 1 | 0.78 | 0.39 |

For therapeutic administration, the object compound (I) and the pharmaceutically acceptable salt thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases, a kind of the compound (I) to be applied, etc. In general amounts between 1 mg and about 4,000 mg or even more per day may be administered to a patient. An average single dose of about 50 mg, 100 mg, 250 mg, 500 mg, 1000 mg, 2000 mg of the object compound (I) of the present invention may be used in treating diseases infected by pathogenic microorganisms.

The following Preparations and Examples are given for the purpose of illustrating the present invention.

Preparation 1

(1) To a solution of benzhydryl 7-[2-(2-tetrahydropyranyl)oxyimino-2-(2-tritylaminothiazol-4-yl)acetamido]-3-chloromethyl-3-cephem-4-carboxylate (syn isomer) (6.5 g) in ethyl acetate (40 ml) was added dropwise a solution of m-chloroperbenzoic acid (1.54 g) in ethyl acetate (10 ml) at 0° C. The mixture was stirred for two hours under ice-cooling and then poured into a mixture of ethyl acetate (50 ml) and water (100 ml). The organic layer was washed with brine and then dried. The solvent was evaporated in vacuo and the residue was pulverized with diisopropyl ether to give benzhydryl 7-[2-(2-tetrahydropyranyl)oxyimino-2-(2-tritylaminothiazol-4-yl)acetamido]-3-chloromethyl-3-cephem-4-carboxylate-1-oxide (syn isomer) (6.90 g).

IR (Nujol): 2940, 1800, 1730, 1680 cm$^{-1}$

NMR (DMSO-$d_6$, δ): 1.10–2.10 (8H, m), 3.87 (2H, s), 4.53 (2H, ABq, J=12Hz), 5.07 (1H, d, J=5Hz), 5.90 (1H, d-d, J=5Hz, 8Hz), 6.84 (1H, s), 7.00 (1H, s), 7.10–7.80 (m), 8.80 (1H, d, J=8Hz)

(2) To a solution of benzhydryl 7-[2-(2-tetrahydropyranyl)oxyimino-2-(2-tritylaminothiazol-4-yl)acetamido]-3-chloromethyl-3-cephem-4-carboxylate-1-oxide (syn isomer) in acetone (100 ml) was added sodium iodide (2.5 g) under ice-cooling. The mixture was stirred for 4.5 hours at the same temperature and then poured into a mixture of ethyl acetate (150 ml) and water (150 ml). The organic layer was separated, washed with brine and dried over magnesium sulfate. The solvent was distilled off. To the residue was added tetrahydrofuran (25 ml) and then 1-methylpyrrolidine (0.52 ml) was added thereto under cooling. The mixture was stirred for 1 hour at the same temperature and then the mixture was poured into ice-water. The resulting precipitates were collected by filtration, dried over phosphorus pentoxide and then subjected to column chromatography on silica gel using methylene chloride and methanol (5:2) as an eluent. The fractions containing the object compound were collected and evaporated to give benzhydryl 7-[2-(2-tetrahydropyranyl)oxyimino-2-(2-tritylaminothiazol-4-yl)acetamido]-3-(1-methyl-1-pyrrolidinio)methyl-3-cephem-4-carboxylate-1-oxide iodide (syn isomer) (1.0 g).

Preparation 2

(1) To a solution of benzhydryl 7-tert-butoxycarbonylamino-3-iodomethyl-3-cephem-4-carboxylate-1-oxide (4.3 g) in dimethylformamide (70 ml) was added 1-methylpyrrolidine (0.63 g) at 0° C. The mixture was stirred for 1.5 hours under ice-cooling and poured into a mixture of ethyl acetate (700 ml) and ice-water (350 ml). The separated organic layer was washed with water, brine and dried over magnesium sulfate. The solvent was distilled off and the residue was pulverized in diisopropyl ether, collected by filtration and dried in vacuo to give powdery benzhydryl 7-tert-butoxycarbonylamino-3-(1-methyl-1-pyrrolidinio)methyl-3-cephem-4-carboxylate-1-oxide iodide (4.3 g).

(2) To a solution of the powder obtained above in dimethylformamide (35 ml) was added phosphorus trichloride (2.0 g) at −20° C. The mixture was stirred for 45 minutes at the same temperature and then was added ice-water (350 ml). The precipitates were collected by filtration and dried over phosphorus pentoxide to give benzhydryl 7-tert-butoxycarbonylamino-3-(1-methyl-1-pyrrolidinio)methyl-3-cephem-4-carboxylate iodide. Furthermore, the same product was obtained from the filtrate by extraction with a mixture of tetrahydrofuran (100 ml) and ethyl acetate (200 ml).

NMR (DMSO-$d_6$, δ): 1.45 (9H, s), 1.70–2.20 (4H), 2.78 (3H, s), 2.82 (2H, ABq), 4.30 (2H), 5.30 (1H), 5.80–6.03 (1H), 7.10 (1H, s), 7.20–7.60 (m)

(3) To a solution of benzhydryl 7-tert-butoxycarbonylamino-3-(1-methylpyrrolidinio)methyl-3-cephem-4-carboxylate iodide (4.42 g) in a mixture of dichloromethane (12 ml) and anisole (4.4 ml) was added trifluoroacetic acid (8.8 ml) under ice-cooling. After stirring for 30 minutes at room temperature, the reaction mixture was gradually poured into diisopropyl ether. The resultant precipitate was collected by filtration, washed with diisopropyl ether and dried over phosphorus pentoxide to give trifluoroacetic acid salt of 7-amino-3-(1-methyl-1-pyrrolidinio)methyl-3-cephem-4-carboxylic acid iodide (2.51 g).

NMR (D$_2$O, δ): 2.00–2.40 (4H, m), 3.98 (3H, s), 3.35–3.70 (4H, m), 3.62 (2H, ABq, J=17Hz), 4.32 (2H, ABq, J=13Hz), 4.82 (1H, d, J=5Hz), 5.19 (1H, d, J=5Hz)

Preparation 3

The following compound was obtained according to a similar manner to that of Preparation 1-(2).

Benzhydryl 7-[2-(2-tetrahydropyranyl)oxyimino-2-(2-tritylaminothiazol-4-yl)acetamido]-3-(1-methyl-1-piperidinio)methyl-3-cephem-4-carboxylate-1-oxide iodide.

Preparation 4

The following compounds were obtained according to a similar manner to that of Preparation 2-(1).
(1) Benzhydryl 7-[2-(2-tetrahydropyranyl)oxyimino-2-(2-tritylaminothiazol-4-yl)acetamido]-3-(1-ethyl-1-pyrrolidinio)methyl-3-cephem-4-carboxylate-1-oxide (syn isomer)
(2) Benzhydryl 7-[2-(2-tetrahydropyranyl)oxyimino-2-(2-tritylaminothiazol-4-yl)acetamido]-3-[1-methyl-1-(3-pyrrolinio)]methyl-3-cephem-4-carboxylate-1-oxide iodide (syn isomer).

IR (Nujol): 3200, 1800, 1720, 1670 cm$^{-1}$
NMR (DMSO-$d_6$, δ): 1.20–2.00 (6H, m), 2.91 (3H, s), 3.5–3.6 (2H, m), 4.0–4.5 (4H+2H+1H, m), 4.6–4.7 (1H, d, J=14Hz), 5.1 (1H+1H, bs), 6.60 (1H, dd, J=5Hz, 8Hz), 6.90 (2H, m), 6.80 (1H, s), 7.00 (1H, s), 7.05–7.60 (15H, m), 8.67 (1H, s), 8.85 (1H, d, J=8Hz)

Preparation 5

(1) To a solution of benzhydryl 7-benzoylamino-3-chloromethyl-3-cephem-4-carboxylate (20 g) in a mixture of dichloromethane (40 ml) and anisole (10 ml) was added trifluoroacetic acid (20 ml) under cooling. After being stirred for two hours at −3°~0° C., the mixture was added dropwise to a mixture of diisopropyl ether (400 ml) and n-hexan (800 ml) at 5° C. The stirring was continued for 15 minutes at the same temperature. The resulting powder was collected by filtration, washed with n-hexan and dried over phosphorus pentoxide to give 7-benzoylamino-3-chloromethyl-3-cephem-4-carboxylic acid.

IR (Nujol): 3270, 1780, 1715, 1650, 1530 cm$^{-1}$

NMR (DMSO-d$_6$, δ): 3.67 (2H, ABq, J=18Hz), 4.60 (2H, s), 5.26 (1H, d, J=5Hz), 5.93 (1H, d-d, J=5Hz, 8Hz), 7.33–7.72 (3H, m), 7.78–8.10 (2H, m), 9.47 (1H, d, J=8Hz)

(2) To a solution of 7-benzoylamino-3-chloromethyl-3-cephem-4-carboxylic acid (14 g) in tetrahydrofuran (280 ml) was added dropwise 1-methylpyrrolidine (16.9 g) over a period of 10 minutes at 10° C. After the mixture was stirred for two hours at 25°~28° C., ethyl acetate (280 ml) was added thereto. The precipitate was collected by filtration, washed with ethyl acetate and diisopropyl ether, dried over phosphorus pentoxide to give 7-benzoylamino-3-(1-methyl-1-pyrrolidinio)methyl-3-cephem-4-carboxylate.

NMR (DMSO-d$_6$, δ): 1.90–2.27 (4H, m), 2.97 (3H, s), 3.02–3.68 (5H, m), 3.90 (1H, d, J=18Hz), 4.03 (1H, d, J=13Hz), 4.95 (1H, d, J=13Hz), 5.21 (1H, d, J=5Hz), 5.78 (1H, dd, J=5Hz, 8Hz), 7.40–7.68 (3H, m), 7.80–8.08 (2H, m), 9.44 (1H, d, J=8Hz)

(3) To a suspension of 7-benzoylamino-3-(1-methyl-1-pyrrolidinio)methyl-3-cephem-4-carboxylate (15 g) in a mixture of dichloromethane (300 ml) and N,N-dimethylaniline (41.7 g) was added dropwise trimethylsilyl chloride (31.2 g) at 5° C. After being stirred for 1 hour at 5°–10° C., the mixture was cooled up to −30° C. and then phosphorus pentachloride (11.9 g), was added thereto. After the mixture was stirred for 1 hour at −20°~−30° C., a mixture of isobutyl alcohol (21.2 g) and 1,3-propanediol (21.8 g) is dichloromethane (150 ml) cooled at −30° C. was added to the reaction mixture. The mixture was stirred for 1 day at room temperature to give a residue, which was collected by filtration, washed with dichloromethane, acetone and diisopropyl ether successively and dried over phosphorus pentoxide to give 7-amino-3-(1-methyl-1-pyrrolidinio)-methyl-3-cephem-4-carboxylate dihydrochloride.

NMR (D$_2$O, δ): 2.07–2.37 (4H, m), 3.01 (3H, s), 3.33–3.67 (4H, m), 3.63 (1H, d, J=18Hz), 3.93 (1H, d, J=18Hz), 4.16 (1H, d, J=13Hz), 4.73 (1H, d, J=13Hz), 5.17 (1H, d, J=5Hz), 5.39 (1H, d, J=5Hz)

(4) To a suspension of 7-amino-3-(1-methyl-1-pyrrolidinio)methyl-3-cephem-4-carboxylate, dihydrochloride (9.8 g) in 1N-hydrochloric acid (39 ml) was added dropwise isopropyl alcohol (46 ml). After being stirred for 1 hour at room temperature, additional isopropyl alcohol (70 ml) was added thereto. The mixture was stirred for further 1 hour at the same temperature to give crystals. The crystals were collected by filtration, washed with isopropyl alcohol and diisopropyl ether and dried over phosphorus pentoxide to give crystalline 7-amino-3-(1-methyl-1-pyrrolidinio)methyl-3-cephem-4-carboxylate dihydrochloride.

mp: 153° C. (dec.)

IR (Nujol): 3300–3450, 1785, 1600–1640, 1540 cm$^{-1}$

NMR (D$_2$O, δ): 2.0–2.43 (4H, m), 2.98 (3H, s), 3.32–3.72 (4H, m), 3.53 (1H, d, J=18Hz), 3.97 (1H, d, J=18Hz), 4.01 (1H, d, J=13Hz), 5.11 (1H, d, J=13Hz), 5.17 (1H, d, J=5Hz), 5.38 (1H, d, J=5Hz)

EXAMPLE 1

To a solution of benzhydryl 7-[2-(2-tetrahydropyranyl)oxyimino-2-(2-tritylaminothiazol-4-yl)acetamido]-3-(1-methyl-1-pyrrolidinio)methyl-3-cephem-4-carboxylate-1-oxide iodide (syn isomer) (1.0 g) in dimethylformamide (8 ml) was added phosphorus trichloride (0.31 g) at −20° C. The mixture was stirred for one hour at the same temperature, and then poured into diethyl ether to give a powder, which was dissolved in tetrahydrofuran and passed through a column of anion-exchange resin "IRA-400" (CF$_3$COO$^-$ form) (Trademark, maker Rohm & Haas) using 90% aqueous tetrahydrofuran as an eluent. The eluates containing the product were concentrated and the resulting precipitates were filtered and dried over phosphorus pentoxide to afford benzhydryl 7-[2-(2-tetrahydropyranyl)oxyimino-2-(2-tritylaminothiazol-4-yl)acetamido]-3-(1-methyl-1-pyrrolidinio)methyl-3-cephem-4-carboxylate trifluoroacetate (syn isomer).

NMR (DMSO-d$_6$, δ): 1.20–2.30 (8H, m), 4.24 (2H, ABq, J=13Hz), 5.23 (1H, d, J=5Hz), 5.70 (1H, dd, J=5, 8Hz), 6.81 (1H, s), 6.92 (1H, s), 7.10–7.90 (m), 9.40 (1H, d, J=8Hz)

EXAMPLE 2

To a solution of benzhydryl 7-[2-(2-tetrahydropyranyl)oxyimino-2-(2-tritylaminothiazol-4-yl)acetamido]-3-(1-methyl-1-pyrrolidinio)methyl-3-cephem-4-carboxylate trifluoroacetate (syn isomer) (0.9 g) in dichloromethane (2.7 ml) were added anisole (0.9 ml) and trifluoroacetic acid (1.8 ml) under ice-cooling. After stirring for 1 hour at room temperature, the mixture was poured into diisopropyl ether (50 ml). The resulting precipitate was collected by filtration, washed with diisopropyl ether, and dissolved in 5% sodium bicarbonate solution. The aqueous solution was adjusted to pH 2.5 with 1N hydrochloric acid, and subjected to column chromatography on non-ionic adsorption resin "HP-20". The desired product was eluted with 5% diisopropyl ether and the eluate was concentrated and lyophilized to give 7-[2-(2-aminothiazol-4-yl)-2-hydroxyiminoacetamido]-3-(1-methyl-1-pyrrolidinio)methyl-3-cephem-4-carboxylate (syn isomer) (0.25 g).

IR (Nujol): 2950, 1770, 1670, 1620 cm$^{-1}$

NMR (D$_2$O, δ): 2.23 (4H, s), 3.56 (4H, s), 3.72 (1H, ABq, J=18Hz), 4.37 (1H, ABq, J=12Hz), 5.38 (1H, d, J=5Hz), 5.88 (1H, d, J=5Hz), 7.09 (1H, s)

EXAMPLE 3

The following compound was obtained according to a similar manner to that of Example 1.

Benzhydryl 7-[2-(2-tetrahydropyranyl)oxyimino-2-(2-tritylaminothiazol-4-yl)acetamido]-3-(1-methyl-1-piperidinio)methyl-3-cephem-4-carboxylate trifluoroacetate (syn isomer).

NMR (DMSO-d$_6$, δ): 1.93–2.17 (6H, m), 1.97–2.23 (8H, m), 2.77 (3H, s), 2.97–3.03 (4H, m), 3.33–3.98 (2H, m), 4.00–4.50 (2H, m), 5.22 (1H, m), 5.32 (1H, d, J=5Hz), 5.60–6.00 (1H, m), 6.73 (1H, s), 7.04 (1H, s), 7.10–7.68 (25H, m), 8.77 (1H, br s), 9.40–9.70 (1H, m)

EXAMPLE 4

The following compound was obtained according to a similar manner to that of Example 2.

7-[2-(2-Aminothiazol-4-yl)-2-hydroxyiminoacetamido]-3-(1-methyl-1-piperidinio)methyl-3-cephem-4-carboxylate (syn isomer).

IR (Nujol): 1770, 1660, 1610, 1530 cm$^{-1}$

NMR (DMSO-d$_6$, δ): 1.07–2.20 (6H, m), 2.95 (3H, s), 2.90–3.60 (5H, m), 3.60–4.60 (2H, m), 4.60–5.30 (1H, m), 5.16 (1H, d, J=5Hz), 5.70 (1H, d-d, J=5Hz, 8Hz), 6.62 (1H, s), 6.87–7.37 (2H, br s), 9.36 (1H, d, J=8Hz), 11.42 (1H, br s)

EXAMPLE 5

To a solution of benzhydryl 7-[2-(2-tetrahydropyranyl)oxyimino-2-(2-tritylaminothiazol-4-yl)acetamido]-3-(1-ethyl-1-pyrrolidinio)methyl-3-cephem-4-carboxylate-1-oxide iodide (syn isomer) (6.25 g) in dimethylformamide (25 ml) was added phosphorus trichloride (1.73 g) at −20° C. The mixture was stirred for half an hour at the same temperature, and then poured into a mixture of dichloromethane and water. The organic layer was separated, washed with water and then brine and evaporated in vacuo. The residue was dissolved in 90% aqueous tetrahydrofuran and passed through a column of anion-exchange resin "IRA-400" (CF$_3$COO$^-$ form) (Trademark, maker Rohm & Haas) using 90% aqueous tetrahydrofuran as an eluent. The eluates containing the product were concentrated and the resulting precipitates were filtered and dried over phosphorus pentoxide to afford benzhydryl 7-[2-(2-tetrahydropyranyl)oxyimino-2-(2-tritylaminothiazol-4-yl)acetamido]-3-(1-ethyl-1-pyrrolidinio)methyl-3-cephem-4-carboxylate trifluoroacetate (syn isomer) (4.0 g).

EXAMPLE 6

The following compound was obtained according to a similar manner to that of Example 5.

Benzhydryl 7-[2-(2-tetrahydropyranyl)oxyimino-2-(tritylaminothiazol-4-yl)acetamido]-3-[1-methyl-1-(3-pyrrolinio)]methyl-3-cephem-4-carboxylate trifluoroacetate (syn isomer).

IR (Nujol): 3400, 1780, 1720, 1650 cm$^{-1}$

EXAMPLE 7

To a solution of benzhydryl 7-[2-(2-tetrahydropyranyl)oxyimino-2-(2-tritylaminothiazol-4-yl)acetamido]-3-(1-ethyl-1-pyrrolidinio)methyl-3-cephem-4-carboxylate trifluoroacetate (syn isomer) (4.0 g) in dichloromethane (12 ml) were added anisole (4 ml) and trifluoroacetic acid (8 ml) under ice-cooling. After stirring for 4 hours at room temperature, the mixture was poured into diisopropyl ether (250 ml). The resulting precipitate was collected by filtration, washed with diisopropyl ether, and dissolved in 5% sodium bicarbonate solution. The aqueous solution was adjusted to pH 2.5 with 1N hydrochloric acid, and subjected to column chromatography on non-ionic adsorption resin "HP-20". The desired product was eluted with 5% isopropyl alcohol and the eluate was concentrated and lyophilized to give 7-[2-(2-aminothiazol-4-yl)-2-hydroxyiminoacetamido]-3-(1-ethyl-1-pyrrolidinio)methyl-3-cephem-4-carboxylate (syn isomer) (0.30 g).

IR (Nujol): 3200, 1770, 1600, 1520 cm$^{-1}$

NMR (DMSO-d$_6$, δ): 1.05–1.50 (3H, m), 1.60–2.30 (4H, m), 5.10 (1H, d, J=5Hz), 5.66 (1H, dd, J=5, 8Hz), 6.60 (1H, s), 7.07 (2H, s), 9.30 (1H, d, J=8Hz)

EXAMPLE 8

The following compound was obtained according to a similar manner to that of Example 7.

7-[2-(2-Aminothiazol-4-yl)-2-hydroxyiminoacetamido]-3-[1-methyl-1-(3-pyrrolinio)]methyl-3-cephem-4-carboxylate (syn isomer).

IR (Nujol): 3250, 1770, 1610 cm$^{-1}$

NMR (DMSO-d$_6$, δ): 3.02 (3H, s), 3.5–3.8 (2H), 4.0–4.4 (4H, m), 4.45, 4.92 (2H, ABq, J=12Hz), 5.08 (1H, d, J=5Hz), 5.65 (1H, dd, J=5, 8Hz), 5.88 (2H, s), 6.58 (1H, s), 9.30 (1H, d, J=8Hz)

EXAMPLE 9

To a mixture of dimethylformamide (5.28 ml) and tetrahydrofuran (15 ml) was added phosphorus oxychloride (6.6 ml) under cooling. The mixture was stirred for 30 minutes under ice-cooling. To the mixture was added a solution of 2-(2-tritylaminothiazol-4-yl)-2-(2-tetrahydropyranyloxyimino)acetic acid (syn isomer) (30.4 g) in tetrahydrofuran (300 ml) with stirring under ice-cooling. The mixture was stirred for 40 minutes at 3° to 5° C. to produce an activated acid solution. On the other hand, to a solution of a salt of 7-amino-3-(1-methyl-1-pyrrolidinio)methyl-3-cephem-4-carboxylate dihydrochloride (20 g) in tetrahydrofuran containing monotrimethylsilylacetamide (107 g) was added at once. The activated acid solution obtained above under cooling at −20° C. and the resulting mixture was stirred for 2 hours at −20° C. to −10° C. To the reaction mixture was added water. The insoluble materials were filtered off and the organic layer in the filtrate was separated. The aqueous layer was saturated with sodium chloride and extracted with ethyl acetate several times. The combined extract was washed with water, aqueous sodium bicarbonate and saturated aqueous sodium chloride successively, and dried over magnesium sulfate. The solvent was distilled off and the residue was subjected to column chromatography on silica gel (250 g) eluting with a mixture of ethyl acetate and isopropyl ether (1:3). The fractions containing the object compound were combined and concentrated under reduced pressure. The residue was triturated in diisopropyl ether to give 7-[2-(2-tritylaminothiazol-4-yl)-2-(2-tetrahydropyranyloxyimino)acetamido]-3-(1-methyl-1-pyrrolidinio)methyl-3-cephem-4-carboxylate (syn isomer) (75.0 g).

EXAMPLE 10

The following compounds were obtained according to a similar manner to that of Example 9 and then Example 2.

(1) 7-[2-(2-Aminothiazol-4-yl)-2-hydroxyiminoacetamido]-3-(1-methyl-2-hydroxymethyl-1-pyrrolidinio)methyl-3-cephem-4-carboxylate (syn isomer).

IR (Nujol): 3200–3300, 1770, 1650, 1605 cm$^{-1}$

NMR (D$_2$O, δ): 1.73–2.63 (4H, m), 3.01 (3H, s), 3.43 (1H, d, J=18Hz), 3.90 (1H, d, J=13Hz), 3.96 (1H, d, J=18Hz), 4.83 (1H, d, J=13Hz), 5.39 (1H, d, J=5Hz), 5.88 (1H, d, J=5Hz), 6.97 (1H, s)

(2) 7-[2-(2-Aminothiazol-4-yl)-2-hydroxyiminoacetamido]-3-(1-methyl-2-carbamoyloxymethyl-1-pyrrolidinio)methyl-3-cephem-4-carboxylate (syn isomer).

IR (Nujol): 1770, 1720, 1650, 1605 cm$^{-1}$

NMR (D$_2$O, δ): 1.77–2.63 (4H, m), 3.07 (3H, s), 3.47, 4.00 (2H, ABq, J=18Hz), 3.27–4.23 (3H, m), 3.93 (1H, d, J=13Hz), 4.32–4.60 (2H, m), 4.87 (1H, d, J=13Hz), 5.38 (1H, d, J=5Hz), 5.88 (1H, d, J=5Hz), 6.97 (1H, s)

EXAMPLE 11

The following compound was obtained from the compound prepared in Example 9 according to a similar manner to that of Example 2.

7-[2-(2-Aminothiazol-4-yl)-2-hydroxyiminoacetamido]-3-(1-methyl-1-pyrrolidinio)methyl-3-cephem-4-carboxylate (syn isomer).

IR (Nujol): 2950, 1770, 1670, 1620 cm$^{-1}$

NMR (D$_2$O, δ): 2.23 (4H, s), 3.56 (4H, s), 3.72 (1H, ABq, J=18Hz), 4.37 (1H, ABq, J=12Hz), 5.38 (1H, d, J=5Hz), 5.88 (1H, d, J=5Hz), 7.09 (1H, s)

Preparation 6

The following compound was obtained according to a similar menner to that of Preparation 5-(2).

7-Benzoylamino-3-[1-methyl-2-(2-hydroxyethyl)-1-pyrrolidinio]methyl-3-cephem-4-carboxylate.

IR (Nujol): 3300, 1770, 1650, 1610, 1580, 1510 cm$^{-1}$

NMR (DMSO-d$_6$,δ): 1.43–2.45 (4H, m), 2.91, 3.08 (total 3H, each S), 3.20–4.20 (10H, m), 4.91, 4.96 (total 1H, each d, J=13Hz), 5.22 (1H, d, J=5Hz), 5.77 (1H, dd, J=5Hz, 8Hz), 7.33–7.75 (3H, m), 7.77–8.12 (2H, m), 9.46 (1H, d, J=8Hz)

Preparation 7

The following compound was obtained according to a similar manner to that of Preparation 5-(3).

7-Amino-3-[1-methyl-2-(2-hydroxyethyl)-1-pyrrolidinio]methyl-3-cephem-4-carboxylate hydrochloride.

NMR (D$_2$O,δ): 1.20–2.50 (4H, m), 3.00, 3.20 (total 3H, each S), 3.86 (2H, ABq, J=18Hz), 3.47–4.23 (8H, m), 4.57 (1H, d, J=13Hz), 5.22 (1H, d, J=5Hz), 5.45 (1H, d, J=5Hz)

EXAMPLE 12

The following compound was obtained according to a similar manner to that of Example 9 and then Example 2.

7-[2-(2-aminothiazol-4-yl)-2-hydroxyiminoacetamido]-3-[1-methyl-2-(2-hydroxyethyl)-1-pyrrolidinio]methyl-3-cephem-4-carboxylate (syn isomer).

IR (Nujol): 3200–3300, 1770, 1660, 1610, 1530 cm$^{-1}$

NMR (D$_2$O,δ): 1.63–2.73 (4H, m), 2.95, 3.16 (total 3H, each S), 3.43 (1H, d, J=18Hz), 3.77 (1H, d, J=18Hz), 3.33–4.10 (8H, m), 4.40–4.83 (1H, m), 5.37 (1H, d, J=5Hz), 5.87 (1H, d, J=5Hz), 6.97 (1H, S)

What we claim is:

1. A cephem compound of the formula:

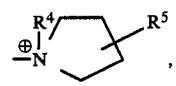

wherein R$^1$ is amino or conventional protected amino, R$^2$ is hydrogen or tetrahydropyranyl, and Y is 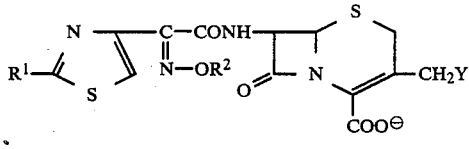

wherein R$^4$ is lower alkyl, and

R$^5$ is hydrogen or lower alkyl substituted with hydroxy or conventional protected hydroxy, and pharmaceutically acceptable salts thereof.

2. A compound of claim 1, wherein R$^1$ is amino or mono-(or di- or tri-)phenyl(lower)alkylamino, and
R$^5$ is hydrogen, hydroxy(lower)alkyl or carbamoyloxy(lower)alkyl.

3. A compound of claim 2, wherein R$^1$ is amino and R$^2$ is hydrogen.

4. A compound of claim 3, wherein Y is

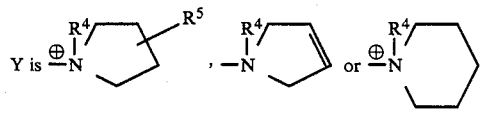

in which R$^4$ and R$^5$ are each as defined in claim 2.

5. A compound of claim 4, which is 7-[2-(2-aminothiazol-4-yl)-2-hydroxyiminoacetamido]-3-(1-methyl-1-pyrrolidinio)methyl-3-cephem-4-carboxylate (syn isomer).

6. A compound of claim 4, which is 7-[2-(2-aminothiazol-4-yl)-2-hydroxyiminoacetamido]-3-(1-ethyl-1-pyrrolidinio)methyl-3-cephem-4-carboxylate (syn isomer).

7. A compound of claim 4, which is 7-[2-(2-aminothiazol-4-yl)-2-hydroxyiminoacetamido]-3-(1-methyl-2-hydroxymethyl-1-pyrrolidinio)methyl-3-cephem-4-carboxylate (syn isomer).

8. A compound of claim 4, which is 7-[2-(2-aminothiazol-4-yl)-2-hydroxyiminoacetamido]-3-(1-methyl-2-carbamoyloxymethyl-1-pyrrolidinio)methyl-3-cephem-4-carboxylate (syn isomer).

9. A compound of claim 4, which is 7-[2-(2-aminothiazol-4-yl)-2-hydroxyiminoacetamido]-3-[1-methyl-2-(2-hydroxyethyl)-1-pyrrolidinio]methyl-3-cephem-4-carboxylate (syn isomer).

10. A compound of claim 3, which Y is

in which R$^4$ is lower alkyl.

11. A compound of claim 10, which is 7-[2-(2-aminothiazol-4-yl)-2-hydroxyiminoacetamido]-3-[1-methyl-1-(3-pyrrolinio)methyl]-3-cephem-4-carboxylate (syn isomer).

12. A compound of claim 3, wherein Y is

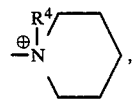

in which R$^4$ is lower alkyl.

13. A compound of claim 12, which is 7-[2-(2-aminothiazol-4-yl)-2-hydroxyiminoacetamido]-3-(1-methyl-1-piperidinio)methyl-3-cephem-4-carboxylate (syn isomer).

14. A pharmaceutical composition comprising, as an active ingredient, an effective amount of the compound of claim 1 or a pharmaceutically acceptable salt thereof in admixture with a suitable carrier.

15. A method for the treatment of bacterial diseases which comprises administering an effective amount of a compound of claim 1 or a pharmaceutically acceptable salt thereof to infected humans or animals.

* * * * *